(12) United States Patent
Kanno (10) Patent No.: US 7,189,350 B2
(45) Date of Patent: *Mar. 13, 2007

(54) METHOD OF STERILIZING MEDICAL INSTRUMENTS

(75) Inventor: Masayuki Kanno, Hanamaki (JP)

(73) Assignee: Kabushiki Kaisha SR Kaihatsu, Hanamaki (JP)

(*) Notice: Subject to any disclaimer, the term of this patent is extended or adjusted under 35 U.S.C. 154(b) by 714 days.

This patent is subject to a terminal disclaimer.

(21) Appl. No.: 10/653,174

(22) Filed: Sep. 3, 2003

(65) Prior Publication Data

US 2004/0120852 A1 Jun. 24, 2004

Related U.S. Application Data

(63) Continuation-in-part of application No. 09/674,712, filed as application No. PCT/JP00/03435 on May 29, 2000, now Pat. No. 6,610,251.

(30) Foreign Application Priority Data

Dec. 27, 1999 (JP) .................................. 11-368643
Mar. 15, 2000 (JP) .................................. 2000-71644

(51) Int. Cl.
*A61L 2/00* (2006.01)

(52) U.S. Cl. ..................... 422/39; 422/28; 422/295; 422/297

(58) Field of Classification Search ............... 422/39, 422/28, 295, 297
See application file for complete search history.

(56) References Cited

U.S. PATENT DOCUMENTS 6,610,251 B1* 8/2003 Kanno ..................... 422/39

FOREIGN PATENT DOCUMENTS

| DE | 43 06 645 A1 | 9/1994 |
|----|----|----|
| EP | 0 397 826 | 11/1990 |
| EP | 0 894 440 A1 | 2/1999 |
| JP | 50-27385 | 3/1975 |
| JP | 3-123604 | 5/1991 |
| JP | 5-207863 | 8/1993 |
| JP | 6-256977 | 9/1994 |
| JP | 07-289220 | 11/1995 |
| JP | 08-089560 | 4/1996 |
| JP | 8-290128 | 11/1996 |
| JP | 9-206044 | 8/1997 |
| JP | 10-024270 | 1/1998 |
| JP | 10-258019 | 9/1998 |
| JP | 11-127827 | 5/1999 |
| JP | 11-276405 | 10/1999 |
| WO | WO 90/06189 | 6/1990 |

* cited by examiner

Primary Examiner—Krisanne Jastrzab
(74) Attorney, Agent, or Firm—Oliff & Berridge, PLC (57) ABSTRACT

A pressure cleaning vessel is connected to a vacuum chamber by way of a connecting pipe in the sterilizing and cleaning equipment that utilizes a supercritical fluid. The objects to be treated are impregnated, for a given period, in the supercritical fluid with which the pressure cleaning vessel has been filled. Thereafter, the connection between the pressure vessel and the vacuum chamber is opened so as to generate sudden bubbling within the vessel as a result of a large pressure difference. Thorough sterilization is achieved at the time when the supercritical fluid having penetrated into bacteria and viruses suddenly explodes and destroys these organisms instantly by vaporization and expansion.

20 Claims, 4 Drawing Sheets

METHOD OF STERILIZING MEDICAL INSTRUMENTS

This is a Continuation-in-Part of application Ser. No. 09/674,712 filed Nov. 16, 2000, now U.S. Pat. No. 6,610, 251 B1, which in turn is a National Stage of PCT/JP00/03435, filed May 29, 2000. The entire disclosure of the prior applications is hereby incorporated by reference herein in its entirety.

TECHNICAL FIELD

This invention relates to a method and the equipment for sterilization by means of a supercritical fluid various medical and dental instruments and appliances which have come in contact with blood and bodily fluids contaminated with bacteria and/or viruses and thus require sterilization to prevent infections when the instruments are reused.

This invention also relates to a method and the equipment for sterilization by means of a supercritical fluid for sterilizing objects such as documents, clothing and medical files contaminated with bacteria and/or viruses or touched by a person contaminated with bacterium and /or viruses.

BACKGROUND OF THE INVENTION

Conventionally, the medical wastes contaminated with infectious bacteria and/or viruses or with excretions from human bodies have been recovered and incinerated by the private services for medical waste disposal because these wastes must be completely burnt at a high temperature to prevent infections and bad smells. Workers in these services collect medical wastes, pile them on the stockyard, and burn them in the incinerator. The waste gases from the incinerator are treated, and the residues from burning are subjected to ash treatment and are disposed at the disposal area. Naturally, it is costly to dispose medical wastes which are not ordinary wastes.

The afore-mentioned medical wastes include low-cost disposables, such as syringes, blood transfusion kits, liquid transfusion kits, dialysis filters, absorbent cotton, but the medical instruments, such as endoscopes, photogastroscopes, operation instruments, costly syringes, and catheters, cannot be similarly disposed. They must be disinfected and sterilized for reuse. Those devices fitted to or into the bodies, such as artificial bones embedded in the bodies, pacemakers, artificial joints, insulin microinfusion devices embedded in the bodies, dentistry materials, dentures, artificial legs, and contact lenses, require the care for reuse similar to the care for the above-described medical instruments, when such devices are fitted again.

Other types of materials considered for reuse include, but are not limited to, patient wear, bed sheets, white coats, doctor and nurse clothing and shoes, personal belongings, gloves and gauze used in operations, sponges and other reusable wastes, and uniforms of paramedics and rescue teams on the ambulances and helicopters. These materials may become contaminated with bacteria and viruses, but it is reasonable for these materials to be reused only if thorough sterilization is cost-justified. If these material can be disposed as ordinary wastes, along with the afore-mentioned low-cost wastes, then there will be a large contribution to the cost reduction.

Hospital tableware, trays, etc., are naturally reused. They should prove to be clean and sterile so as to avoid serving as a mediator of infections.

Some materials may be shared or used by multiple persons. For example, medical records and charts are often circulated among numerous people such as the hospital staff and must remain intact as permanent records. These materials must be cleaned and sterilized without damaging or erasing the vital information that they contain. Further examples include, but are not limited to, care-taking materials, library materials and books, lockers and storage boxes. These materials may become contaminated with bacteria and viruses yet they are not ordinarily considered disposable items.

Meanwhile, medical instruments equipped with soft rubber components must naturally be cleaned and thorough disinfection or sterilization is required to prevent infections when these instruments coming in contact with blood and other bodily fluids are to be reused safely. Such instruments include artificial hearts for embedded use, blood filters, blood dialysis instruments, adsorption columns, and various endoscopes inserted into the body, all of which have extended tubes of flexible rubber or polymer materials serving as blood channels. These rubber or polymer materials must be disinfected or sterilized by all means in spite of the difficulties in the disinfection or sterilization of such materials.

The treated objects must not have residues of a toxic gas or other substances used for disinfection or sterilization.

Cleaning is necessary treatment preceding disinfection or sterilization. By cleaning, it is aimed at removing microorganisms and not killing them, and it is also meant that organic substances and foreign substances, such as blood, tissues, and feces, are eliminated from the objects to be sterilized.

Full cleaning (physical treatment) eliminates microbes and organic substances adhered to endoscopes to a considerable extent. The disinfecting effects of some disinfectants are affected by blood and bodily fluids, and it is highly meaningful to wash the objects before disinfection.

Disinfection is defined as selective killing of specific microbes and achieving loss of infectivity. Technically, it is achieved by boiling, UV radiation, or the use of disinfectants. Disinfection excludes those ordinarily existing bacteria having no pathogenicity but strong resistance to disinfectants.

Sterilization refers to eradication or elimination of all microbes from an object. There are such methods as high-pressure steam sterilization, gas sterilization by means of ethylene oxide, etc., and a filtering method utilizing membrane filters.

The status quo of sterilization will be described below, while attention is paid to the case of endoscopes.

Endoscopes have their origin to simple gastroscopes of a hard type. Then fiberscopes were invented and further improved to electronic endoscopes. These changes in design have been promoted by the necessity for sophisticated diagnoses and medical care which required complex systems. These endoscopes as a result of technological innovation are of structures not suitable for cleaning or sterilization. The most important factor has been the capability as medical instruments.

The Disinfection Committee of Japan Gastroenterological Endoscopy Technicians Society divided the risks of infections caused by medical instruments into three groups of high, intermediate, and low. The endoscopes for use in digestive organs were classified as belonging to the group of intermediate risk, which means a necessity of such a high level of disinfection that endoscopes must be sterile, except for bacterial spores. The reason for this level is that the mucous membranes of digestive tracts can be resistant to the infections caused by bacterial spores, but these membranes are susceptible to infections with pathogenic microorganisms such as tubercle bacillus or viruses.

Since endoscopes are costly and endoscopy is used frequently, many of Japanese medical institutions follow a policy that after patients have been checked for the existence of any infectious disease before the endoscopic test, those with no infection are tested with the endoscope first of all, while those with some infection are tested later in the day. In such a case, thorough cleaning and sterilization are not conducted for each patient with no infection, but imperfect cleaning and sterilization methods are used. Endoscopes are thoroughly cleaned and sterilized only when they have been used for the infected patients.

Since this method allows for many tests in a short time, it looks as though the method can be justified. In fact, however, the pathogens which can be checked by this method are limited to only HBV, HCV, syphilis spirochete, HIV (only at a part of institutions), and the like. No other infections can be checked. Test results are incomplete, as obvious from, for instance, AIDS people with HIV showing a so-called window period in their initial period of infection. For 6–8 weeks of the window period, HIV antibody is negative, and yet those with AIDS actually discharge this virus.

The risk of infections caused by insufficient and inappropriate cleaning and sterilization after such checking is proved by the reports of infections with *H. pylori*. Recently, there were cases of hepatitis of type C as caused from endoscopy. Actually there are cases of infections which have dodged their way through the prior checking procedure.

During a test, the endoscope comes in contact with mucous membranes of the gastrointestinal tracts. If endoscopes are contaminated with pathogenic organisms, there are dangers of infections. Major infectious pathogens include HBV, HCV/HIV, syphilis spirochete, tubercle bacillus, *Pseudomonas aeruginosa*, MRSA, *H. pylori*, and many others. These organisms have varied levels of pathogenicity, infectivity, and resistance to disinfectants. It is necessary, therefore, to conduct a high level of sterilization for endoscopes, giving due consideration to the risk of cross-infections with known and unknown bacteria and viruses.

1) Contamination and Cleanability of Endoscopes

Endoscopes have a complex structure, but the portion, in which cleaning and sterilization are involved, consists of relatively simple components of a long and narrow rubber tube and the control section having convex and concave shapes. The portions apt to get contamination include firstly the tip of biopsy/suction channel, the tip of air/water-sending channel, and the outside of inserted portion; and secondly the control section, although light guide and connectors are less contaminated. Meanwhile, stains are not so easy to remove from the biopsy/suction channel, especially the gaps therein formed by connectors and assemblies, and from the control section. The largest problem in cleaning endoscopes lies in the biopsy/suction channel.

2) Endoscope Materials

The curved portion of an endoscope is made of glass fiber and CCD and is coated with rubber. Because of this coating, the endoscopes are susceptible to heat, and get damage from heat unless they are cleaned generally at or below 40–55° C. (temperature differs by makers). It is impossible to clean them in boiling water even in a short time.

The first choice of disinfectant for use in the cleaning of endoscopes is glutaraldehyde, which is less damaging to the materials and effective to a wide variety of pathogenic organisms.

In its guideline, the Japan Gastroenterological Endoscopy Technicians Society advises doctors to regard all patients as having an infection and to clean the endoscope by washing it fully and then impregnating it in a 2% glutaraldehyde solution at least for 10 minutes.

Glutaraldehyde is toxic, irritant, and allergic. It invades human bodies from the eyes by scattering, through the skin by touch, and through the respiratory tract by inhalation, and there is the possibility that this substance may cause dermatitis, conjunctivitis, rhinitis, and hypersensitivity in paranasal sinuses.

In order to minimize the amount of this substance sticking to the body, the endoscopist wears a mask, a pair of gloves, plastic gown, and goggles for protection at the time of disinfection. Disinfection must be conducted in a well-ventilated area by utilizing a closed disinfecting container. Special attention should be paid to avoid the disinfectant liquid from scattering.

Among the instruments and materials for use in operations, the articles having high heat resistance are mostly sterilized with high-pressure steam. Those articles less resistant to heat and the precision instruments are sterilized with ethylene oxide (EtO) gas. At present, EtO sterilization is indispensable due to its effectiveness and convenience, but this method has a problem of carcinogenicity caused by the residues of toxic chlorine gas on the sterilized articles, because Cl gas is added for higher sterilization. The toxicity includes tissue toxicity and hemolytic toxicity. The EtO gas is reported to remain especially on the polyvinyl chloride products for a long time, and the amount of residue is proportional to the amount of plasticizer contained in such products. The amount of remaining EtO gas can be reduced by leaving the instruments standing in air for a predetermined period before use or by forced ventilation using an aerator. Concerning the EtO sterilization, there are stringent standards now in effect on the concentration of aerial EtO in the working environment.

As described above, it is difficult for prior art methods to thoroughly sterilize bacteria and viruses in a short time. Even if sterilization has been achieved, the prior art methods have to face the secondary troublesome problems of wastewater treatment and removal of disinfecting substances remaining on the medical instruments.

Recent threats to health and welfare include, for example, spore forming bacteria, such as exosporium-covered *Bacillus subtilis* and *Bacillus anthracis*. It is unanimously recognized by world medical societies that *Bacillus anthracis* is so highly heat-resistant and drought resistant that it does not die at 120° C. or lower.

Additional threats to health and welfare include the arrival of new or previously unrecognized pathogens that can cause dangerous and/or lethal outbreaks of infection in the general public such as, for example, human immunodeficiency virus (HIV), SARS virus and West-Nile virus. Sometimes the pathogen is unknown or not readily identified.

Therefore, the object of this invention is to achieve the thorough eradication of pathogenic bacteria and viruses in a short period of sterilization, a high level of cleaning treatment with no need of drying process, and the finish cleaning with no stain of hazardous chemicals.

More particularly, the object of this invention is to provide a method and equipment for sterilizing those medical instruments which are less resistant to heat because of the rubber parts used in their soft components and thus are disadvantageous for disinfection and sterilization and yet require thorough sterilization before reuse for the prevention of infections. Thorough sterilization, which is effective not only for bacteria but also for infectious viruses, can be achieved by this method easily without any deterioration of the rubber material and with no problem of harmful residues of strong chemicals. Furthermore, cleaning, sterilization, and drying steps can be completed in a period as short as 30 minutes so that this cleaning procedure can be repeated any number of times a day.

An additional object of this invention is to provide a method and equipment for sterilizing items such as documents, letters and stationary contaminated with bacteria and/or viruses, or touched by a person contaminated with bacteria and/or viruses. Other items that can be sterilized include the clothes of doctors and nurses, care-taking materials, patients' files, documents at the office counter work, storage lockers and book storerooms.

More particularly, an object of this invention is to provide a method and equipment for sterilizing objects that may be contaminated with HIV, SARS virus or West-Nile virus, or that may have been touched by a person contaminated with HIV, SARS virus or West-Nile virus. A further object of this invention is to provide a method and equipment for sterilizing objects that may be, or thought to be, contaminated with true fungi and spore-forming bacteria, such as, for example, exosporium-covered *Bacillus subtilis* and *Bacillus anthracis*, or that may have been touched by a person contaminated with such microorganisms.

Another object of this invention is to provide a method and equipment for sterilizing materials that cannot be opened other than in person (e.g., letters directed to VIPS, government or military officials). These materials can be sterilized without opening or otherwise ruining their contents. Sterilization equipment according to this invention can be installed at post offices or at office counters.

DISCLOSURE OF THE INVENTION

The method of sterilizing medical instruments according to this invention is characterized by the steps of connecting a pressure cleaning vessel to a vacuum chamber by way of a connecting pipe in the sterilizing and cleaning equipment which utilizes a supercritical fluid; impregnating the objects to be cleaned, for a given period, in the supercritical fluid with which the pressure cleaning vessel has been filled; and thereafter opening the connection between the pressure vessel and the vacuum chamber or releasing the supercritical fluid to the outside in a moment, so as to generate sudden bubbling within the vessel as a result of a large pressure difference. Thorough sterilization is achieved at the time when the supercritical fluid having penetrated into bacteria and viruses explodes and destroys these organisms instantly by its power of vaporization and expansion. Finish cleaning work is then achieved by the cleaning action of the supercritical fluid with no need of drying.

The above-described operation causes the following phenomenon to occur.

Figure 4:
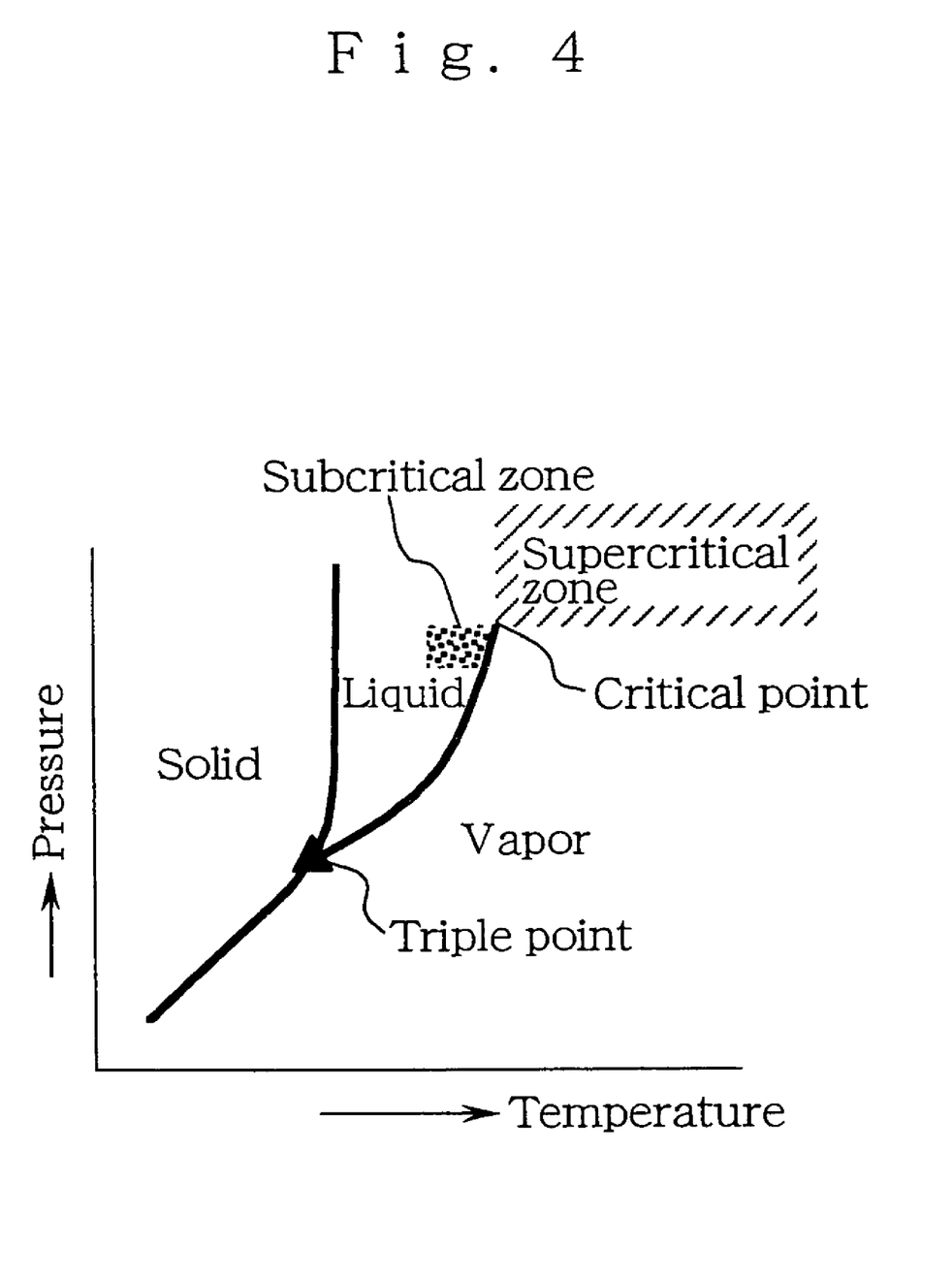
FIG. 4 is a graph showing the phase diagram of a pure substance.

As shown FIG. 4, which is the phase diagram of a pure substance, the supercritical fluid near its critical point can be regarded as a high-density fluid put under the conditions of a pressure and a temperature higher than those at the critical point. Such a supercritical fluid has the unique characteristics, namely:

(1) A large change in density can be obtained with slight changes in pressure and temperature. As the solubility of a substance is generally in proportion to the density, the changes only in pressure and temperature give a large change in solubility; and (2) The density of a supercritical fluid is similar to that of a liquid, but the fluid is less viscous (lower than the viscosity of a gas) and more diffusive than the liquid. Therefore, the fluid is more advantageous than the liquid in the aspect of the fluid transfer.

There are many proposals taking advantage of these characteristics skillfully in the cleaning of semiconductor substrates or in the extraction of various components.

Subcritical fluids have also the aforementioned characteristics of the supercritical fluid. The subcritical fluid refers to a fluid in the region right to this side of the critical point in the pressure-temperature phase diagram. The compressed liquid and the gas coexist in a subcritical fluid in a saturated (balanced) state. In that point, the fluid in this region is distinguished from the supercritical fluid.

After the supercritical fluid has penetrated the bacterial cells and the inside of viruses (owing to the above-described high diffusivity) in the pressure cleaning vessel, the connection is then opened between the pressure vessel and the vacuum chamber which are in the "supercritical zone." The pressure of the supercritical fluid inside bacterial cells and viruses is suddenly brought down to the critical level, and the fluid expands (going toward a balanced state), thus forming bubbles of the saturated gas.

Since this sudden expansion destroys the bacterial cells and viruses, thorough sterilization is achieved.

In the case of $CO_2$, for example, the supercritical $CO_2$ fluid suddenly makes a shift down to a lower pressure and temperature, and at the critical point (31° C., 70M) the fluid becomes a liquefied gas. Owing to this sudden expansion, the fluid destroys the bacterial cells and viruses.

This means that it has become possible to sterilize thoroughly at a low temperature those medical instruments and other materials which are susceptible to high temperatures and cannot be sterilized at a high temperature. For example, materials contaminated with *Bacillus anthracis* can be sterilized at 80° C. using the supercritical $CO_2$ sterilization equipment.

Furthermore, the objects to be cleaned receive a high level of cleaning action due to the above-described solubility.

As well known, this cleaning can make drying unnecessary. It takes only a short time to perform this treatment based on the utilization of the characteristics of the supercritical fluid. As described above, the sterilizing action according to this invention is caused by the expansion of the fluid and not by the efficacy of a strong chemical having sterilizing power. Therefore, if a harmless gas (such as carbon dioxide gas) is selected, no processing for safety precautions is required in its reuse.

The gases which can be used for this invention include ethylene gas used as a sterilizing gas, ethanol and other alcohols having sterilizing power, nitrogen oxide, ethane, and propane, in addition to carbon dioxide.

The rubber used in medical instruments tends to be deteriorated on contact with $CO_2$ gas. In the case of endoscopes using rubber parts for smooth movements, the rubber surfaces are advantageously coated with a Teflon or aluminum layer in a double structure when $CO_2$ is used as the supercritical fluid. This coating prevents $CO_2$ from penetrating the rubber, and keeps the rubber flexible.

Meanwhile, the cleaning equipment of this invention is characterized by a closed recycling system which comprises:

(a) A pressure cleaning vessel provided with a cleaning basket supported in midair within the pressure cleaning vessel for accommodating the objects to be treated, a plurality of nozzles to emit spray of compressed liquid directly onto the objects for the purpose of pretreatment before the finish cleaning, and a vacuum chamber of a similar capacity placed above, and connected to, the pressure cleaning vessel, and further provided with an agitator consisting of an impeller disposed on the bottom of the cleaning vessel and sound wave generators directed toward the impeller and disposed on the side walls of the cleaning vessel;

(b) A pressure recovery vessel equipped with a means of temperature control and placed below the pressure cleaning vessel to receive the used cleaning liquid after the cleaning process, and having a drain cylinder detachably suspended from under the pressure recovery vessel;

(c) A high density liquefied gas supply cylinder placed at a position higher than the pressure cleaning vessel, and equipped with a means of temperature control, and connected to the pressure cleaning and recovery vessels by the lines for gas flow through the upper portions of these vessels and the cylinder so as to receive overhead gas from the pressure vessels; and (d) An entrainer vessel connected to a point halfway on the feed line between the high density liquefied gas supply cylinder and the pressure cleaning vessel;

Wherein the closed recycling system is characterized by enabling the overhead gas to flow through the upper portions of these compressed liquid-sending and/or -receiving vessels.

The above pressure cleaning vessel can also be designed so as to omit the vacuum chamber and instead, to have the pressure cleaning vessel provided with an opening in the ceiling, through which gas inside the vessel is released in an instant to outside.

Concerning the above equipment, the solvent feedstock cylinder can be placed at a position higher than the pressure cleaning vessel and equipped with a means of temperature control, and can be connected to the pressure cleaning by the line for gas flow through the upper portions of this vessel and the cylinder so as to receive overhead gas from the pressure cleaning vessel.

The cleaning equipment of this invention is also characterized by a closed recycling system which comprises:

(a) A pressure cleaning vessel provided with a cleaning basket supported in midair within the pressure cleaning vessel for accommodating the objects to be treated, a plurality of nozzles to emit spray of compressed liquid directly onto the objects for the purpose of pretreatment before the finish cleaning treatment, and a vacuum chamber of a similar capacity placed above, and connected to, the pressure cleaning vessel, and further provided with an agitator consisting of an impeller disposed on the bottom of the cleaning vessel and sound wave generators directed toward the impeller and disposed on the side walls of the cleaning vessel;

(b) A pressure recovery vessel equipped with a means of temperature control and placed under the pressure cleaning vessel to receive the used cleaning liquid after the cleaning process, and having a drain cylinder detachably suspended from under the pressure recovery vessel;

(c) A high density liquefied gas supply cylinder equipped with a means of temperature control, and connected to the pressure cleaning and recovery vessels by the lines for gas flow through upper portions of these vessels and the cylinder so as to receive overhead gas from the pressure vessels; and (d) A pressure pump for compressed liquid transfer and an entrainer vessel connected to the points halfway on the feed line between the high density liquefied gas supply cylinder and the pressure cleaning vessel;

Wherein the closed recycling system is characterized in that the feed from the feedstock cylinder is sent to the high density liquefied gas cylinder by way of a compressor.

Instead of utilizing the agitating mechanism consisting of an impeller and sound wave generators, a pipe for the transfer of the supercritical fluid from the feedstock cylinder can be connected to the pressure cleaning vessel at its bottom to introduce the gaseous feed into the liquefied gas and thereby to generate bubbling adequate for finishing cleaning.

THE BEST EMBODIMENTS FOR THE PRACTICE OF THIS INVENTION

Figure 1:
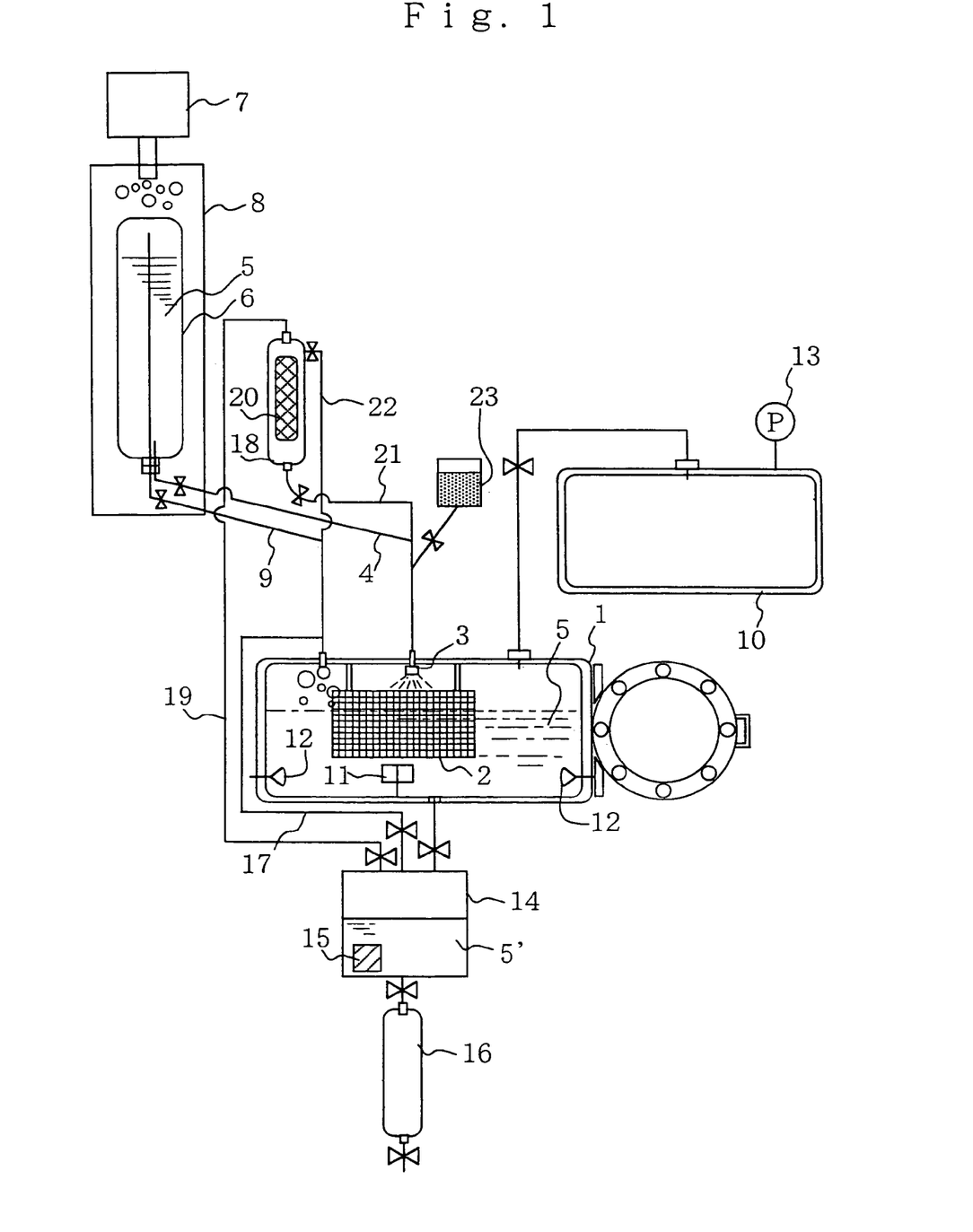
FIG. 1 is a schematic diagram showing an embodiment of the equipment according to this invention.
Figure 2:
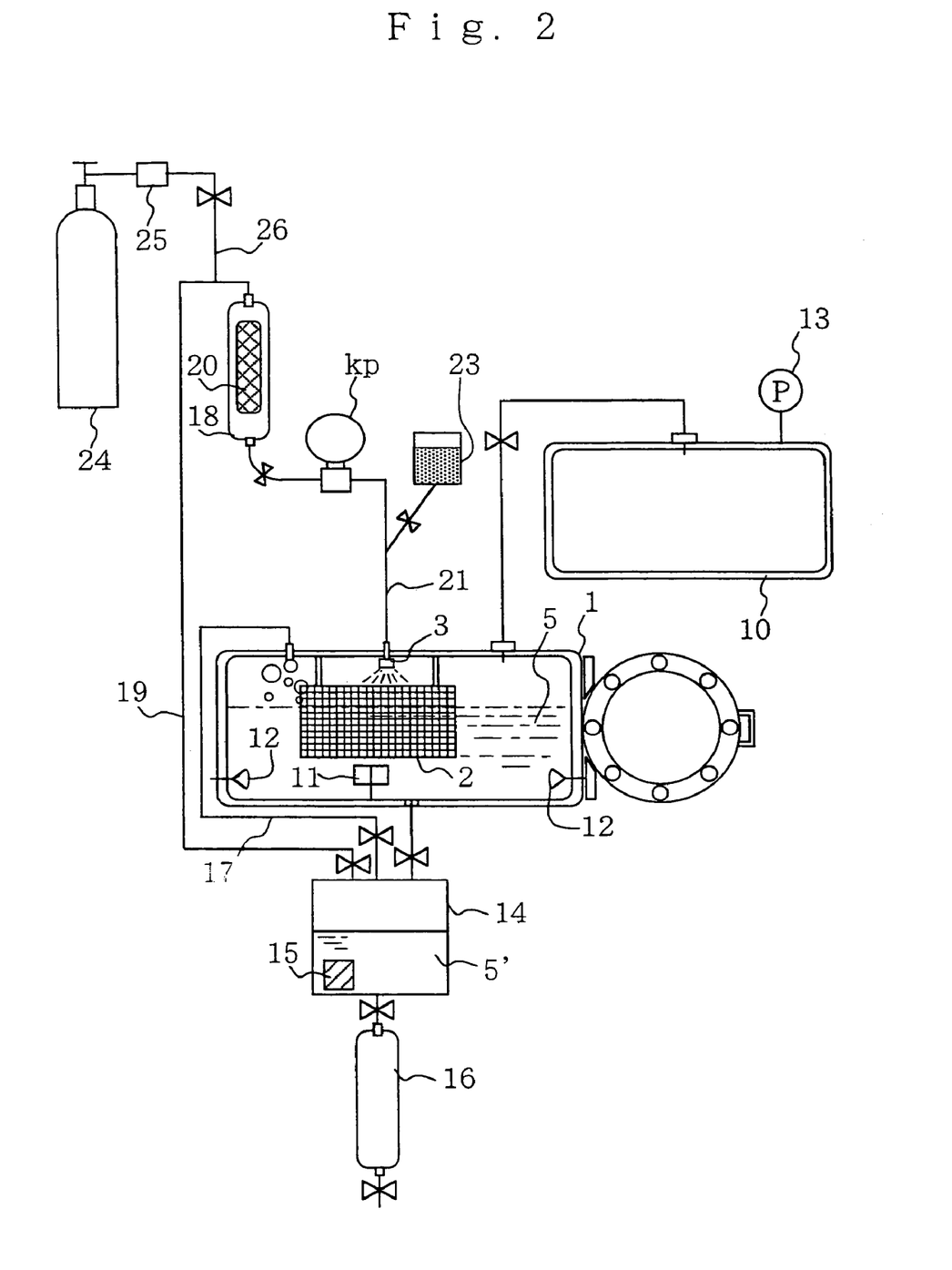
FIG. 2 is a schematic diagram showing another embodiment of the equipment according to this invention.

This invention is further described in details, now referring to the attached drawings, wherein FIGS. 1 and 2 show different embodiments of this invention.

As shown in FIG. 1, the pressure cleaning vessel 1 has the cleaning basket 2 for accommodating the objects to be treated, and the basket 2 is supported in midair within the vessel directly under a plurality of nozzles 3 (more than one being necessary for effective cleaning). In this way, cleaning is carried out after sterilization by injecting jet streams of the compressed liquid 5 from the nozzles 3 onto the objects in the basket 2. The impact energy of the jet stream injection is effective for forcibly peeling contaminants off the objects at the time of finish cleaning.

The solvent feedstock cylinder 6 is filled with a high density liquefied gas. Compressed liquid 5 is supplied from the cylinder 6 to the pressure cleaning vessel 1 through pressure pipe 4 and the nozzles 3. According to the embodiment shown in FIG. 1, the solvent feedstock cylinder 6 is accommodated inside a box 8 which is provided with a temperature controller 7 to control the temperature of the solvent. The cylinder 6 is placed at a position higher than the pressure cleaning vessel 1, and the compressed liquid 5 is sent by gravity fall, utilizing the difference in height. (The temperature controller 7 sets the cylinder 6 at a higher temperature than in the pressure cleaning vessel 1 to make sure of solvent transfer based also on the difference in vapor pressures. The feed transfer is further backed up by the gas flow through the pressure pipe 9 linking between upper portions of the cylinder 6 and the vessel 1.)

On the pressure cleaning vessel 1 is placed the vacuum chamber 10 of a similar capacity to perform effective, sudden vaporization and expansion of the fluid. When the connection is opened between the pressure vessel 1 and the vacuum chamber 10, the supercritical fluid, which has penetrated into bacterial cells and viruses, goes through the process of vaporization and expansion as a result of a large pressure difference to destroy bacteria and viruses. At that time, the supercritical fluid or compressed liquid 5 packed in the pressure cleaning vessel 1 expands and generates sudden bubbling within the vessel 1.

The high and low positions of the vacuum chamber 10 and the pressure cleaning vessel 1 can be advantageously utilized to bring the liquid from the vacuum chamber 10 back to the pressure cleaning vessel 1 for reuse at the next time of sterilization.

An impeller 11 is disposed on the bottom of the cleaning vessel and directly below the cleaning basket 2. In addition, sound wave generators 12 are disposed on the side walls of the cleaning vessel 1 and are directed toward the impeller 11. Even stronger agitation is thus available due to the synergistic effect of forced agitation and cavitation created by the impeller 11 which is rotated by the projection of ultrasonic energy. The finish cleaning of objects can be carried out under quite strong agitation while the objects are completely immersed in the compressed liquid 5 which is also supplied from the entrainer vessel and fills the cleaning vessel 1.

Such members as rubber tube used in medical instruments tend to deteriorate (as the nature of urethane rubber) when it comes in contact with the supercritical $CO_2$ fluid. Therefore, the surfaces of rubber materials must be coated with a Teflon or aluminum layer to keep the surface resistant to the supercritical $CO_2$ fluid.

A pressure recovery vessel 14 is placed at a position lower than the pressure cleaning vessel 1 to receive the used cleaning liquid 5'. The liquid 5' is received quickly due to the gravity fall from a higher level, a difference in vapor pressures, and the gas flow between these vessels. In addition, the solvent used in finish cleaning can be eliminated quickly. The recovery vessel 14 is provided with an inside temperature controller 15, and has a drain cylinder 16 detachably suspended from under the pressure recovery vessel 14. It is possible therefore that after receiving contaminants to the full, the drain cylinder 16 is cut from the recycling system, taken off to empty the content at a given place, and then connected again to the recycling system.

The pressure cleaning vessel 1 is connected with the pressure recovery vessel 14 by a pipe 17 to allow for the gas flow between these vessels. The vapor phase in the pressure recovery vessel 14 is connected by the pipe 19 with the upper portion of the high density liquefied gas supply cylinder 18, which is placed at a position higher than the pressure cleaning vessel 1 and serves as a storage means for the closed recycling system. The solvent in the pressure recovery vessel 14 is heated by the temperature controller 15, and the vaporized solvent is sent to the cylinder 18 placed at the higher position due to the difference in vapor pressures.

The cylinder 18 has an internal temperature controller 20 which cools and liquefies the aforementioned vaporized solvent. The pipe 21 extends front under the cylinder 18 and is connected to the pipe 4 and then to the nozzles 3 of the pressure cleaning vessel 1. The afore-mentioned entrainer vessel 23 is connected to this pipe 4. Another pipe 22 for gas flow is provided to supplement this gravity fall transfer. At that time, the temperature controller 20 is heated so that the gravity fall is supplemented by the setting of temperature difference.

FIG. 2 shows another embodiment of the sterilization equipment of a type in which the closed recycling system also comprises a pressure pump KP for compressed liquid transfer, which is connected to a point halfway on the feed line between the high density liquefied gas supply cylinder 18 and the pressure cleaning vessel 1; and a compressor 25 for feed transfer, which is connected to the feed line 26 at a point between the $CO_2$ feedstock cylinder 24 and the high density liquefied gas cylinder 18.

Figure 3:
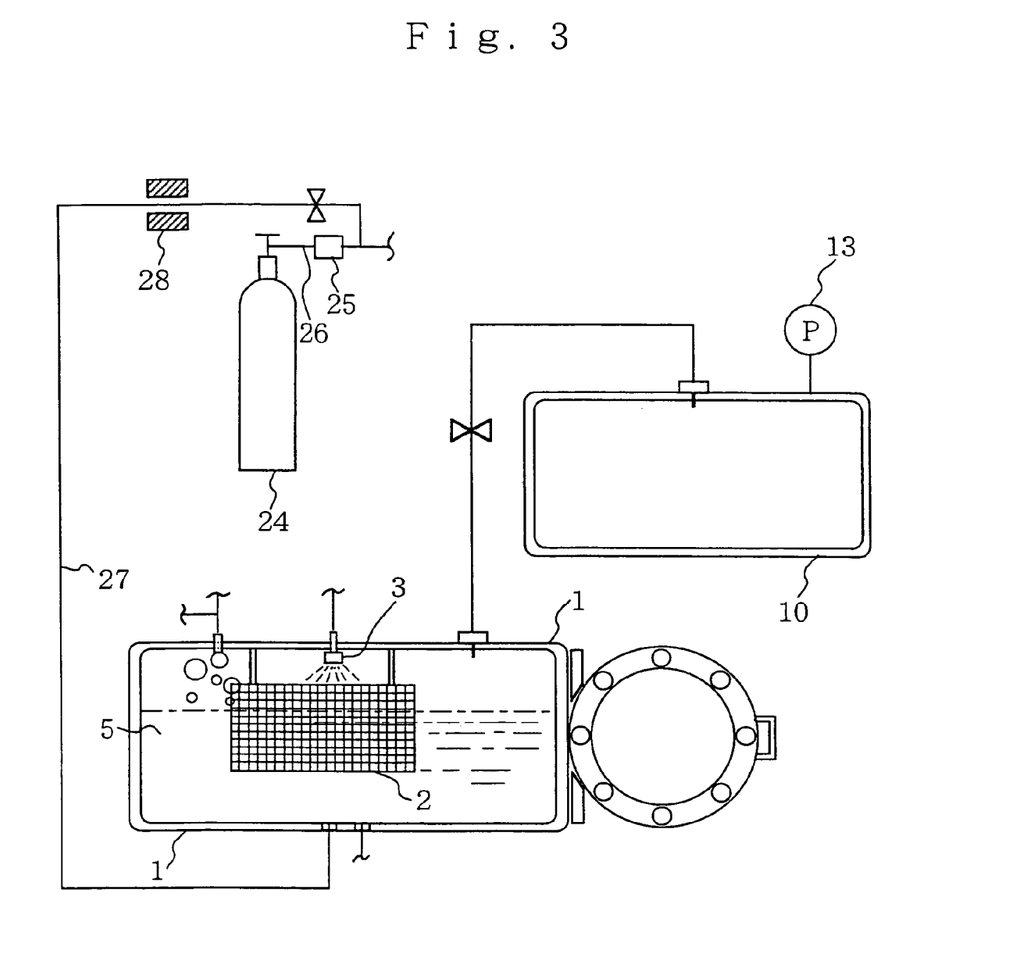
FIG. 3 is a schematic diagram showing the major portions of the equipment for sterilization and finish cleaning of this invention.

FIG. 3 shows still another embodiment of the sterilization equipment wherein agitation for finish cleaning can be accomplished reasonably in the pressure cleaning vessel 1.

In this embodiment, the pipe 26 extends from under the cylinder 24, passes through the compressor 25, and is connected to a sideline 27 which in turn is connected to the bottom of the pressure cleaning vessel 1. A heater 28 is disposed halfway on this sideline to enable the gas in the supercritical zone to be supplied.

Even without the impeller 11 and sound generators 12 that make the inside of the vessel 1 much complicated, it is possible to generate the bubbling adequate for finish cleaning when the "gas" is introduced into the "liquid" through the bottom of the pressure cleaning vessel 1.

It is simply preferred that the fluid to be introduced is supercritical to a relatively higher extent than the fluid inside the pressure cleaning vessel 1. Thus, there may be a case where the fluid inside the pressure cleaning vessel 1 is a supercritical fluid that is not a "liquid."

POSSIBILITY OF INDUSTRIAL UTILIZATION

This invention, having such a constitution as described above, practically enables various medical goods to be thoroughly sterilized and cleaned for reuse. Not only that, but the method according to this invention is also effective in sterilizing, for the safety of wearers, those articles fitted for the first time to or into human bodies.

From an equipment point of view, it is possible to provide extensive sterilization and cleaning without drying, which are performed in a short time in such a place as hospital room, by employing multiple units according to this invention utilizing a supercritical fluid.

Antibiotic-resistant bacteria are said to require special stringent measures for the prevention and control of infections in hospitals. Since the method according to this invention can be used to sterilize such resistant bacteria thoroughly, this method is good news for those seeking to take safety measures as early as possible.

As a way to make effective use of this equipment, the medical goods not intended for reuse can be sterilized in this equipment to turn these goods into the less costly rank of ordinary wastes.

It is also possible to manufacture the pressure cleaning vessel of such a large size as to accommodate hospital beds for sterilization.

According to this method, one can take advantage that there is no drying process. Some personal letters, that cannot be opened other than in person (e.g., letters contaminated with anthrax bacteria directed to VIPS or government or military officials) can be put into the described sterilization equipment installed at post offices or at the office counters. Only the anthrax bacteria die inside the letters and the contents of the letters can remain indelible.

In practice, this method can be used for the sterilization and cleaning of various materials, such as artificial bones and artificial blood vessels to be embedded into human bodies, medical devices such as dializing instruments and pacemakers to be attached to human skin, and surfaces of endoscope components. Generally it is quite difficult to sterilize gauze, cotton, and porous materials such as sponge, which are used to wipe and clean the human skin. Since the supercritical fluid used in accordance with this invention completely penetrates and sterilizes the inside of these materials, the reuse of these materials can be 100% guaranteed.

It is also possible to provide effective sterilization of objects such as documents, letters and stationary contaminated with HIV, SARS virus or West-Nile virus or touched by a person contaminated with HIV, SARS virus or West-Nile virus.

What is claimed is:

1. A method of sterilizing objects utilizing a supercritical fluid, comprising the steps of:
   (1) connecting a pressure cleaning vessel and a vacuum chamber to each other by way of at least one connecting pipe carrying said supercritical fluid;
   (2) impregnating the objects to be sterilized, for a given period, in said supercritical fluid with which said pressure cleaning vessel has been filled; and
   (3) thereafter opening the connection between said pressure cleaning vessel and said vacuum chamber so as to generate sudden bubbling within said vessel as a result of a pressure difference;
   wherein thorough sterilization is achieved when said supercritical fluid having penetrated into bacteria and viruses explodes and destroys these organisms instantly by its power of vaporization and expansion; and
   wherein finish cleaning work is also achieved at the same time by the cleaning action of said supercritical fluid.

2. A method of sterilizing objects utilizing a supercritical fluid, comprising the steps of:
   (1) providing an opening in a ceiling of a pressure cleaning vessel;
   (2) impregnating the objects to be sterilized, for a given period, in said supercritical fluid with which said pressure cleaning vessel has been filled;
   (3) thereafter releasing the supercritical fluid fully through said opening in the ceiling of said pressure cleaning vessel, so as to generate sudden bubbling within said vessel as a result of a pressure difference;
   wherein thorough sterilization is achieved when said supercritical fluid having penetrated into bacteria and viruses explodes and destroys these organisms instantly by its power of vaporization and expansion; and
   wherein finish cleaning work is also achieved at the same time by the cleaning action of said supercritical fluid.

3. The method according to claim 1, wherein said objects are documents, letters or stationary.

4. The method according to claim 2, wherein said objects are documents, letters or stationary.

5. The method according to claim 1, wherein said objects are contaminated by SARS virus or touched by a person contaminated by SARS virus.

6. The method according to claim 2, wherein said objects are contaminated by SARS virus or touched by a person contaminated by SARS virus.

7. The method according to claim 1, wherein said objects are contaminated by spore-forming bacteria.

8. The method according to claim 2, wherein said objects are contaminated by spore-forming bacteria.

9. The method according to claim 5, wherein said spore-forming bacteria are exosporium-covered *Bacillus subtislis* or *Bacillus anthracis*.

10. The method according to claim 6, wherein said spore-forming bacteria are exosporium-covered *Bacillus subtislis* or *Bacillus anthracis*.

11. The method according to claim 1, wherein said thorough sterilization is achieved at a temperature more than about 80° C.

12. The method according to claim 2, wherein said thorough sterilization is achieved at a temperature more than about 80° C.

13. The method according to claim 1, wherein cleaning action is performed by the forced agitation of liquefied gas after the vaporization and expansion of said supercritical fluid.

14. The method according to claim 2, wherein cleaning action is performed by the forced agitation of liquefied gas after the vaporization and expansion of said supercritical fluid.

15. The method according to claim 1, wherein said cleaning action is performed by the bubbling generated when the supercritical fluid, which is supercritical to a relatively higher extent than the supercritical fluid inside the pressure cleaning vessel, is introduced into said pressure vessel through its bottom.

16. The method according to claim 2, wherein said cleaning action is performed by the bubbling generated when the supercritical fluid, which is supercritical to a relatively higher extent than the supercritical fluid inside the pressure cleaning vessel, is introduced into said pressure vessel through its bottom.

17. The method according to claim 1, wherein said objects are medical appliances, dental materials and metal objects configured to be inserted into a body of a patient.

18. The method according to claim 2, wherein said objects are medical appliances, dental materials and metal objects configured to be inserted into a body of a patient.

19. The method according to claim 1, wherein said objects are contaminated by SARS virus, HIV virus or West Nile virus or touched by a person contaminated by SARS virus, HIV virus or West Nile virus.

20. The method according to claim 2, wherein said objects are contaminated by SARS virus, HIV virus or West Nile virus or touched by a person contaminated by SARS virus, HIV virus or West Nile virus.

* * * * *

UNITED STATES PATENT AND TRADEMARK OFFICE
CERTIFICATE OF CORRECTION

PATENT NO. : 7,189,350 B2  Page 1 of 1
APPLICATION NO. : 10/653174
DATED : March 13, 2007
INVENTOR(S) : Masayuki Kanno It is certified that error appears in the above-identified patent and that said Letters Patent is hereby corrected as shown below:

In the claims, please amend the following:
    In claim 9 (col. 12, line 6):
    Amend the word: "subtislis" to --subtilis--.

In claim 10, (col. 12, line 10):
    Amend the word: "subtislis" to --subtilis--.

Signed and Sealed this

Fifth Day of June, 2007

JON W. DUDAS
*Director of the United States Patent and Trademark Office*